United States Patent
Yasuda et al.

(10) Patent No.: US 6,187,945 B1
(45) Date of Patent: *Feb. 13, 2001

(54) PROCESS FOR PRODUCING CYANOBENZYL COMPOUNDS

(75) Inventors: Hiroshi Yasuda; Masatoshi Murakami, both of Kanagawa (JP)

(73) Assignee: Showa Denko K.K., Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/448,994

(22) Filed: Nov. 24, 1999

Related U.S. Application Data

(60) Provisional application No. 60/163,392, filed on Nov. 4, 1999.

(30) Foreign Application Priority Data

Nov. 26, 1998 (JP) .................................................. 10-335139

(51) Int. Cl.$^7$ .................................................. C07C 255/00
(52) U.S. Cl. ........................ 558/416; 558/423; 558/425
(58) Field of Search ................................. 558/416, 423, 558/425

(56) References Cited

U.S. PATENT DOCUMENTS 4,283,565   8/1981   Bernhardt et al. .

FOREIGN PATENT DOCUMENTS 0 596 684 A1   5/1994   (EP) .

OTHER PUBLICATIONS

Tomoo Mizugaki, et al., Highly Chemoselective Reduction of Aldehyde Function Catalyzed by Polymer–Bound $Rh_6$ Cluster Complex under Water–Gas Shift Reaction Conditions, Tetrahedron Letters, vol. 38, No. 17, 1997, pp. 3005–3008.

F.F. Blicke et al., Basic–alkyl Esters of p–(Aminoalkyl-)–benzoic Acids, Journal of the American Chemical Society, vol. 65, No. 12, 1943, pp. 2281–2284.

John Baldwin Shoesmith, et al., Polarity Effects in the Isomeric omega–Bromoxylenes and Isomeric Iodotoluenes, Journal of the Chemical Society, pp. 2278–2283, 1924.

European Search Report dated Feb. 11, 2000.

Balakrishnan, P. et al, $^{17}O$ NMR Spectroscopy: Unusual Substituent Effects in para–Substituted Benzyl Alcohols and Acetates, Tetrahedron Letters, vol. 25, No. 2, pp 169–172, 1984.

*Primary Examiner*—Joseph K. McKane
*Assistant Examiner*—Joseph Murray
(74) *Attorney, Agent, or Firm*—Sughrue, Mion, Zinn, Macpeak & Seas, PLLC

(57) ABSTRACT

An industrially advantageous process for producing cyanobenzyl compounds under mild conditions from relatively easily available cyanobenzylamine having a cyano group on the benzene ring or a compound thereof which is ring-substituted with a chlorine atom, a fluorine atom, etc. The process for producing a cyanobenzyl compound includes transforming an aminomethyl group of a cyanobenzylamine compound into a hydroxymethyl group, a halogenomethyl group, or an acyloxymethyl group without causing damage to a cyano group on the benzene ring. The transformation may be carried out by use of nitrosonium ions.

18 Claims, No Drawings

PROCESS FOR PRODUCING CYANOBENZYL COMPOUNDS

CROSS REFERENCE TO RELATED APPLICATIONS

This application is an application filed under 35 U.S.C. §111(a) claiming benefit pursuant to 35 U.S.C. §119(e)(i) of the filing date of Provisional Application No. 60/163,392 filed Nov. 4, 1999 pursuant to 35 U.S.C. §111(b).

FIELD OF THE INVENTION

The present invention relates to a process for producing cyanobenzyl compounds, and more particularly to a process for producing cyanobenzyl compounds represented by formula (II). Cyanobenzyl compounds are important intermediates for producing chemical products such as pharmaceuticals, agrochemicals, liquid crystals, and monomers of functional polymers.

BACKGROUND OF THE INVENTION

Several processes for producing cyanobenzyl compounds are already known.

1. Cyanobenzyl alcohol compounds

Exemplary processes for producing p-cyanobenzyl alcohol, a typical cyanobenzyl alcohol compound, are as follows.

p-Cyanobenzyl alcohol is synthesized through reduction of a p-cyanobenzoic acid ester or p-cyanobenzaldehyde using a reducing agent formed of a hydride compound such as sodium borohydride (Kikugawa, Y., *Chem. Pharm. Bull,* 24 (1976) 1059; and Hilborn, J. W., et al., *J. Am. Chem. Soc.,* 116 (1994) 3337). Alternatively, p-cyanobenzaldehyde is reduced through water gas shift reaction in the presence of a rhodium cluster-on-polymer catalyst (Kaneda, K., et al., *Tetrahedron Letters,* 38 (1997) 3005).

2. Cyanobenzyl halide compounds

An exemplary process for producing p-cyanobenzyl chloride, a typical cyanobenzyl halide compound, is as follows.

p-Cyanobenzyl chloride is synthesized through monochlorination of p-tolunitrile (*J. Am. Chem. Soc.,* 65 (1943) 2282: L. Blicke).

3. Cyanobenzyl acyloxy compounds

Exemplary processes for producing p-cyanobenzyl acetate, a typical cyanobenzyl acyloxy compound, are as follows.

p-Cyanobenzyl acetate is synthesized through reaction of p-cyanobenzyl chloride and sodium acetate in an alcohol solvent (Banse, *Chem. Ber.,* 27 p2171 (1894)). Alternatively, p-cyanobenzyl acetate is synthesized through acetylation of p-cyanobenzyl alcohol (A. L. Baumstark, et al., *Tetrahedron Letters,* 25 p169 (1984)).

The above processes for producing p-cyanobenzyl compounds have disadvantages as described below.

1. p-Cyanobenzyl alcohol

When reduction is carried out by use of a reducing agent formed of a hydride, such an expensive reagent is required in an amount greater than the stoichiometric amount, to thereby produce a large amount of waste. When reduction is carried out using hydrogen, an expensive rhodium catalyst is employed. Thus, both processes are economically disadvantageous.

2. p-Cyanobenzyl chloride

Hazardous chlorine gas is used for chlorinating p-tolunitrile, and selectivity of monochlorination is insufficient.

3. p-Cyanobenzyl acetate p-Cyanobenzyl chloride or p-cyanobenzyl alcohol serving as a raw material is not easily available as a general-purpose raw material.

As described above, the synthesis of p-cyanobenzyl compounds by use of a conventionally known technique is cumbersome, and production of high-purity compounds is difficult. In addition, raw materials such as a p-cyanobenzoic acid ester, p-cyanobenzaldehyde, and p-tolunitrile are not easily available. Thus, the above processes are unsatisfactory for production of cyanobenzyl compounds at high yield and high purity on an industrial scale.

In view of the foregoing, the present invention is directed to provision of an industrially advantageous process for producing cyanobenzyl compounds under mild conditions from relatively easily available cyanobenzylamine having a cyano group on the benzene ring or a compound thereof which is ring-substituted with a chlorine atom, a fluorine atom, etc. (hereinafter these compounds may generally be referred to as "cyanobenzylamine compounds").

SUMMARY OF THE INVENTION

The present inventors have found that the above object is attained through transformation of an aminomethyl group ($-CH_2NH_2$) of a cyanobenzylamine compound which serves as a starting material into a hydroxymethyl group, a halomethyl group, or an acyloxymethyl group without causing damage to a cyano group on the benzene ring. The present invention has been accomplished on the basis of this finding.

Accordingly, embodiments of the present invention are as follows:

(1) a process for producing a cyanobenzyl compound comprising transforming an aminomethyl group of a cyanobenzylamine compound into a hydroxymethyl group, a halomethyl group, or an acyloxymethyl group without damaging a cyano group on the benzene ring;

(2) a process for producing a cyanobenzyl compound according to embodiment (1), wherein an aminomethyl group is transformed into a hydroxymethyl group, a halomethyl group, or an acyloxymethyl group by use of nitrosonium ions;

(3) a process for producing a cyanobenzyl compound according to embodiment (2), wherein a nitrite salt is used under acidic conditions in order to generate nitrosonium ions;

(4) a process for producing a cyanobenzyl compound according to embodiment (2), wherein a nitrogen oxide is used in order to generate nitrosonium ions;

(5) a process for producing a cyanobenzyl compound according to any one of embodiments (1) to (4), wherein the reaction is carried out in the presence of a polar solvent;

(6) a process for producing a cyanobenzyl compound according to embodiments (1) or (2), wherein the cyanobenzylamine compound is represented by the following formula (I):

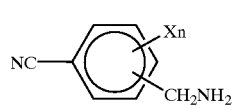

wherein each of $-CH_2NH_2$ and $-X$ represents a substituent on the benzene ring; the $-CH_2NH_2$ group is bonded to the m- or the p- position with respect to the —CN group; X represents a chlorine atom or a fluorine atom; n is an integer between 0 and 4 inclusive; and when n is 2 or more, the plurality of X's may be identical to or different from one another, and the cyanobenzyl compound is represented by the following formula (II):

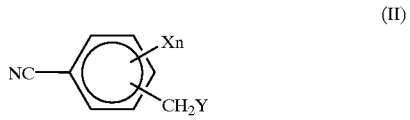

(II)

wherein each of —X and —$CH_2Y$ represents a substituent on the benzene ring; the —$CH_2Y$ group is bonded to the m- or the p- position with respect to the —CN group; X represents a chlorine atom or a fluorine atom; n is an integer between 0 and 4 inclusive; and when n is 2 or more, the plurality of X's may be identical to or different from one another; Y represents a hydroxyl group, a fluorine atom, a chlorine atom, a bromine atom, an iodine atom, or an acyloxy group represented by —OCOR, wherein R represents a $C_1$–$C_8$ alkyl group, an alkenyl group, or an aryl group;

(7) a process for producing a cyanobenzyl compound according to embodiment (6), wherein the cyanobenzylamine compound represented by formula (I) is p-cyanobenzylamine or m-cyanobenzylamine, and the cyanobenzyl compound represented by formula (II) is a corresponding p-cyanobenzyl alcohol or m-cyanobenzyl alcohol;

(8) a process for producing a cyanobenzyl compound according to embodiment (6), wherein the cyanobenzylamine compound represented by formula (I) is p-cyanobenzylamine or m-cyanobenzylamine and the cyanobenzyl compound represented by formula (II) is a corresponding p-cyanobenzyl chloride, p-cyanobenzyl bromide, m-cyanobenzyl chloride, or m-cyanobenzyl bromide;

(9) a process for producing a cyanobenzyl compound according to embodiment (6), wherein the cyanobenzylamine compound represented by formula (I) is p-cyanobenzylamine or m-cyanobenzylamine and the cyanobenzyl compound represented by formula (II) is a corresponding p-cyanobenzyl acetate or m-cyanobenzyl acetate; and

(10) a cyanobenzyl compound which is produced through the process as recited in embodiments (1) or (2), wherein an aminomethyl group of a cyanobenzylamine compound is transformed into a hydroxymethyl group, a halomethyl group, or an acyloxymethyl group without causing damage to a cyano group on the benzene ring.

DESCRIPTION OF THE PREFERRED EMBODIMENTS

The reaction process according to the present invention is carried out through the following steps: placing a solvent, a cyanobenzylamine compound, a nitrite salt or a nitrogen oxide, and if necessary a nucleophilic species in a reactor, the nucleophilic species being placed under acidic conditions for producing a cyanobenzyl alcohol compound; elevating the temperature of the thus-formed mixture to the reaction temperature with stirring; and heating the mixture for a predetermined time with stirring.

Typically, suitable materials for the reactor employed for the reaction include glass and acid-resistant metal. No particular limitation is imposed on the reaction pressure, and the reaction is typically carried out under atmospheric pressure.

Taking the transformation of p-cyanobenzylamine into a corresponding p-cyanobenzyl compound as an example, reactions occurring in conceivable reaction paths in the present invention are described below. The reaction modes of other compounds of the present invention should be considered to be similar.

Reaction Scheme [I]

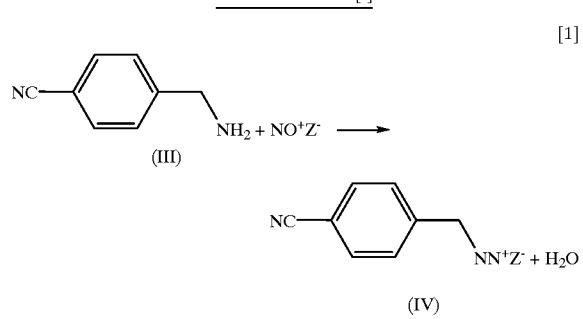

[1]

Reaction Scheme [II]

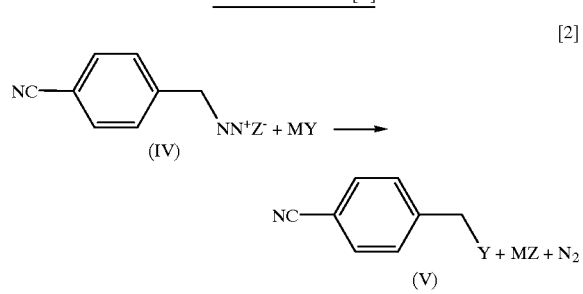

[2]

p-Cyanobenzylamine compound (III) is reacted with nitrosonium ion species ($NO^+Z^-$), to thereby form diazonium compound (IV) (reaction scheme [1]: the reaction may be referred to as a diazotization reaction). Nucleophilic species (MY) present in the reaction system is reacted with compound (IV), to thereby form p-cyanobenzyl compound (V) (reaction scheme [2]: hereinafter the reaction may be referred to as a substitution reaction).

Accordingly, use of nucleophilic species (MY) in which M is a hydrogen atom and Y is a hydroxyl group; i.e., water, yields p-cyanobenzyl alcohol, as described in the following, Reaction Scheme [3].

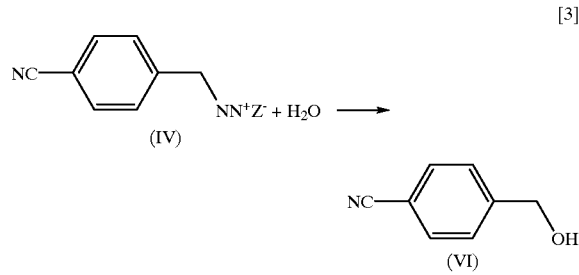

[3]

Use of nucleophilic species (MY) in which M is a hydrogen atom or an alkali metal or alkaline earth metal atom and Y is a halogen atom yields a cyanobenzyl halide compound, as described in the following Reaction Scheme [4].

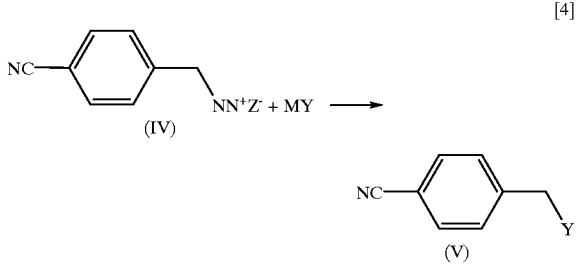

[4]

Alternatively, use of nucleophilic species (MY) in which M is a hydrogen atom and Y is an acyloxy group; i.e., a carboxylic acid, yields a cyanobenzyl acyloxy compound as described in the following Reaction Scheme [5].

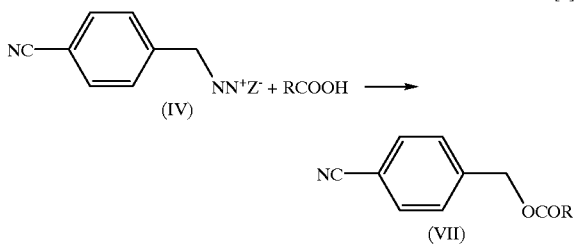

[5]

In the case the solvent used has any activity as a nucleophilic species for the target cyanobenzyl compound, addition of the agent for nucleophilic species is not necessary.

In the case in which the counter anion (Z⁻) of diazonium ion (IV) is a halide ion or an acyloxy anion (RCOO⁻), each of the anion species serves as a nucleophilic species to cause intramolecular reaction, to thereby yield a cyanobenzyl halide compound or a cyanobenzyl acyloxy compound as a by-product, respectively. Since the anion species are derived from the acids which are employed in the present reaction, the acids need to be chosen in accordance with the target cyanobenzyl compounds.

When a cyanobenzyl alcohol compound is synthesized, reaction between a cyanobenzylamine compound and nitrosonium ions must be carried out in a polar organic solvent in the presence of an acid, or in an aqueous solution in the presence of an acid having low nucleophilicity such as sulfuric acid, phosphoric acid, or nitric acid.

The cyanobenzylamine compounds which are employed in the present reaction are now described. Among unsubstituted cyanobenzylamine compounds, p-cyanobenzylamine and m-cyanobenzylamine are preferred. These two amines can be synthesized easily through reduction of one nitrile group of terephthalonitrile or isophthalonitrile, respectively, as described in Japanese Patent Publication No. 40-10133.

The substituted compounds of the cyanobenzyl compounds are next described. No particular limitation is imposed on the substituents, and any substituent may be bonded so long as it is inert to the reaction of the present invention. Examples include alkyl groups and alkoxy groups, with $C_1$–$C_6$ alkyl groups and $C_1$–$C_6$ alkoxy groups being preferred. Of these, halo-substituted cyanobenzylamine compounds will be described as exemplary particularly preferred compounds. Chlorinated cyanobenzylamine compounds such as 4-cyano-2,3,5,6-tetrachlorobenzylamine and 3-cyano-2,4,5,6-tetrachlorobenzylamine can be synthesized easily on a large scale through reduction of one nitrile group of a chlorinated terephthalonitrile compound such as tetrachloroterephthalonitrile or a chlorinated isophthalonitrile compound such as tetrachloroisophthalonitrile, with tetrachloroterephthalonitrile or tetrachloroisophthalonitrile being obtained through chlorination of terephthalonitrile or isophthalonitrile, respectively. Fluorinated cyanobenzylamine compounds such as 4-cyano-2,3,5,6-tetrafluorobenzylamine and 3-cyano-2,4,5,6-tetrafluorobenzylamine can be synthesized easily through reduction of one nitrile group of a fluorinated terephthalonitrile compound such as tetrafluoroterephthalonitrile or a fluorinated isophthalonitrile compound such as tetrafluoroisophthalonitrile, with tetrafluoroterephthalonitrile or tetrafluoroisophthalonitrile being obtained through fluorination of chlorinated terephthalonitrile compounds such as tetrachloroterephthalonitrile or chlorinated isophthalonitrile compounds such as tetrachloroisophthalonitrile, respectively.

Nitrosonium ions which are employed in the reaction of the present invention will next be described.

No particular limitation is imposed on the step for generating nitrosonium ion compounds in the reaction of the present invention, and nitrosonium ion compounds may be synthesized separately or generated in the reaction system during reaction.

Nitrosonium salt compounds, which are ionic crystalline solids, are known as nitrosonium ion species having relatively high stability and have known compositions. Examples include $NOClO_4$, $NOSO_3F$, $NOHSO_4$, $NOSCN$, $NOBF_4$, $NOPF_4$, $NOAsF_4$, $NOSbF_4$, $NOFeCl_4$, and $NOMoF_6$. These nitrosonium salts as such may be used in the reaction.

In the present invention, the nitrosonium salt compound is preferably used in an amount of 1–5 by mol ratio based on the cyanobenzylamine compound.

Nitrosonium ions may be generated from a nitrite salt which is used under acidic conditions or from a nitrogen oxide serving as a source.

When a nitrite salt is used, the reaction is carried out under acidic conditions.

In the reaction of the present invention, a nitrite salt such as sodium nitrite or potassium nitrite may be used as a source for generating nitrosonium ions. The nitrite salt is preferably used in an amount of 1–10 by mol ratio based on the cyanobenzyl compound. The acid which is used for generating a nitrosonium salt is used in an amount at least equimol based on the nitrite salt, preferably in an amount by mol of 2 times or more. Inorganic or organic protonic acids may be used as the above acids. Examples of inorganic acids include hydrochloric acid and hydrobromic acid. Examples of organic acids include carboxylic acids such as acetic acid, propionic acid, and trifluoroacetic acid; and sulfonic acids such as methanesulfonic acid and trifluoromethanesulfonic acid. Of these, carboxylic acids such as acetic acid and trifluoroacetic acid having a low boiling point are preferred in that such acids also serve as solvents.

In the reaction of the present invention, a nitrogen oxide may be used as a source for generating nitrosonium ions. In the present invention, the term "nitrogen oxide" refers to a compound exclusively consisting of nitrogen and oxygen. Examples of nitrogen oxides include nitrogen monoxide, dinitrogen trioxide, nitrogen dioxide, dinitrogen tetraoxide, and dinitrogen pentoxide. A mixture of nitrogen oxides; e.g., dinitrogen monoxide and nitrogen dioxide, may also be used. In addition, since an enormously large amount of nitrogen oxide exhaust gas produced during oxidation of cyclohexane with nitric acid in the Nylon industry may also be used in the present invention, an economically advantageous process can be designed. The nitrogen oxide must be used in an amount of 1 mol or more per mol of a cyanobenzyl compound.

The nucleophilic species which is used in the substitution reaction of diazonium compound (IV) during the reaction of the present invention will be described.

When a cyanobenzyl alcohol compound is synthesized, water is used as a nucleophilic species. In the case of reaction between a cyanobenzylamine compound and a nitrosonium salt, no additional water serving as a nucleophilic species is required, since water is by-produced in the reaction.

When a cyanobenzyl halide compound is synthesized, a halide compound is used as a nucleophilic species. Examples of halide compounds include hydrogen halides such as hydrogen chloride and hydrogen bromide; alkali metal salts such as sodium chloride, potassium chloride, sodium bromide, and potassium bromide; and alkaline earth metal salts such as calcium chloride and magnesium bromide. The halide compound is required in an amount of at least equimol based on the cyanobenzylamine compound. Furthermore, an aqueous solution such as an aqueous hydrochloric acid used as a solvent may be served as a nucleophilic species.

When a cyanobenzyl acyloxy compound is synthesized, a carboxylic acid compound is used as a nucleophilic species. Examples of carboxylic acid compounds which can be used include aliphatic carboxylic acids having a $C_1$–$C_8$ alkyl group such as acetic acid and propionic acid; carboxylic acids having an alkenyl group such as methacrylic acid; and benzoic acids containing an aromatic moiety having an aryl group, such as benzoic acid and toluic acid. The carboxylic acid compound is used in an amount of at least equimol based on the cyanobenzylamine compound. Of these, aliphatic carboxylic acids such as acetic acid which also serves as a solvent are particularly preferred.

When the reaction is carried out in a homogeneous solvent system, a polar solvent is preferably employed. Examples include water, a polar organic solvent, and a mixture of water/polar organic solvent. Specific examples of organic solvents include polar amides such as formamide and dimethylformamide; sulfur-containing solvents such as dimethyl sulfoxide and sulforane; imidazolidones such as 1,3-dimethyl-2-imidazolidinone; ethers such as 1,2-dimethoxyethane and diglyme; acid anhydrides such as acetic anhydride and propionic anhydride; and organic carboxylic acids such as acetic acid, trifluoroacetic acid, and propionic acid.

The reaction may also be carried out in an aqueous-organic two-phase system. In this case, any organic solvent may be used so long as the solvent can dissolve a cyanobenzylamine compound (which is a raw material) and a cyanobenzyl compound (which is a product of the reaction).

In the reaction, the solvent is preferably used in an amount by weight 5 to 100 times that of the cyanobenzylamine compound.

The reaction temperature preferably falls within the range of −30° C. to 200° C., more preferably 0° C. to 130° C.

The reaction time varies depending on the composition of the solvent, and a time of 10 minutes to 10 hours is preferred.

EXAMPLES

The present invention will next be described in more detail by way of examples, which should not be construed as limiting the invention thereto. Unless otherwise indicated, all parts, percents, ratios and the like are by weight.

In the Examples hereunder, the following methods are employed for analysis.

High-Performance Liquid Chromatographic Analysis Conditions for Example 1

Column: Shodex DE-513L+precolumn

Eluent: Water/acetonitrile/acetic acid=2250/750/15 (ml) sodium 1-octanesulfonate 6.45 g Conditions: Flow rate, 1 ml/minute UV 254 nm Column oven 40° C.

Gas Chromatographic Analysis Conditions for Examples 2–8

Column: HP-5

(30 m capillary column, inner diameter: 0.32 mm)

Carrier: Helium 1.7 cc/minute

Split ratio: 50

Detector: FID

Analysis conditions: injection at 300° C.
     100° C. (10 minutes)→10° C./minute
     (elevation)→300° C.
     detection at 300° C.

Example 1 p-Cyanobenzylamine (26.2 g), sodium nitrite (20.8 g), and dimethyl sulfoxide (200 ml) were mixed, and the mixture was vigorously stirred at room temperature (about 20 to 30° C.). Trifluoroacetic acid (45.6 g) was added dropwise to the mixture over a one hour period. After completion of addition, the mixture was further allowed to react at 100° C. for one hour. The reaction mixture was analyzed by use of high performance liquid chromatography, to thereby obtain proportions (on the mol basis) of predominant reaction products: p-cyanobenzyl alcohol:p-cyanobenzaldehyde:p-cyanobenzoic acid= 72:18:10. Dimethyl sulfoxide was removed through distillation under vacuum, and water (300 ml) was added to the residue. Sodium carbonate was added to the thus-formed solution, to thereby adjust pH to 8. The resultant aqueous solution was subjected to extraction with toluene (300 ml×2). Toluene was removed through distillation under reduced pressure, and the resultant solution was subsequently distilled under vacuum, to thereby obtain 16.2 g of p-cyanobenzyl alcohol (bp. 175–178° C./1.5 kPa) (yield 61%). The purity of the product was 98%.

Example 2 m-Cyanobenzylamine (13.2 g), sodium nitrite (10.4 g), and dimethylformamide (100 ml) were mixed together, and the mixture was vigorously stirred at room temperature. Trifluoroacetic acid (22.8 g) was added dropwise to the mixture over one hour. After completion of addition, the mixture was further allowed to react at 100° C. for one hour. For the subsequent process, the procedure of Example 1 was repeated, to thereby obtain 6.9 g of m-cyanobenzyl alcohol (bp. 128–130° C./400 Pa) (yield 52%). The purity of the product was 98%.

Example 3 p-Cyanobenzylamine (13.2 g), water (54 g), and toluene (20 g) were mixed, and the mixture was stirred with cooling with ice. Concentrated sulfuric acid (14.7 g) was added to the mixture. Subsequently, a 20 wt % aqueous solution (44.9 g) of sodium nitrite was added dropwise to the mixture over one hour. The mixture was stirred at the same temperature for four hours. For the subsequent process, the procedure of Example 1 was repeated, to thereby obtain 6.8 g of p-cyanobenzyl alcohol (yield 51%). The purity of the product was 98%.

Example 4 p-Cyanobenzylamine (13.2 g), potassium bromide (23.8 g), water (18 g), and methylene chloride (18 g) were mixed, and the mixture was stirred with cooling with ice. Concentrated sulfuric acid (29.4 g) was added to the mixture. Subsequently, a 20 wt % aqueous solution (51.8 g) of sodium nitrite was added dropwise to the mixture over one hour. The mixture was stirred at the same temperature for four hours. Further, sodium thiosulfate was added to the mixture, and the resultant mixture was stirred at room temperature for one hour. Gas chromatographic analysis revealed that the yield of p-cyanobenzyl bromide was 64%.

Example 5 m-Cyanobenzylamine (13.2 g), potassium bromide (23.8 g), water (18 g), and methylene chloride (18 g) were mixed, and the mixture was stirred with cooling with ice. Concentrated sulfuric acid (98% by weight) (29.4 g) was added to the mixture. Subsequently, a 20 wt % aqueous solution (51.8 g) of sodium nitrite was added dropwise to the mixture over one hour. The mixture was stirred at the same temperature for four hours. Further, sodium thiosulfate was added to the mixture, and the resultant mixture was stirred at room temperature for one hour. Gas chromatographic analysis revealed that the yield of m-cyanobenzyl bromide was 57%.

Example 6 p-Cyanobenzylamine (13.2 g), sodium chloride (11.7 g), water (18 g), and 1,2-dichloroethane (25 g) were mixed, and the mixture was stirred with cooling with ice. Concentrated sulfuric acid (29.4 g) was added to the mixture. Subsequently, a 20 wt % aqueous solution (51.8 g) of sodium nitrite was added dropwise to the mixture over one hour. The mixture was stirred at the same temperature for four hours. Further, sodium thiosulfate was added to the mixture, and the resultant mixture was stirred at room temperature for one hour. Gas chromatographic analysis revealed that the yield of p-cyanobenzyl chloride was 48%.

Example 7 p-Cyanobenzylamine (13.2 g), water (18 g), and methylene chloride (18 g) were mixed, and the mixture was stirred with cooling with ice. Acetic acid (18 g) was added to the mixture. Subsequently, a 20 wt % aqueous solution (51.8 g) of sodium nitrite was added dropwise to the mixture over a one hour period. The mixture was stirred at the same temperature for four hours. The reaction mixture was subjected to extraction with methylene chloride, and the organic solvent was concentrated. Water was added to the concentrated solution, and the residual organic solvent was removed through distillation, to thereby obtain 14.7 g of p-cyanobenzyl acetate (yield 84%). The purity of the product was 98%.

Example 8 m-Cyanobenzylamine (13.2 g), water (18 g), and 1,2-dichloroethane (22 g) were mixed, and the mixture was stirred with cooling with ice. Acetic acid (18 g) was added to the mixture. Subsequently, a 20 wt % aqueous solution (51.8 g) of sodium nitrite was added dropwise to the mixture over a one hour period. The mixture was stirred at the same temperature for four hours. The reaction mixture was subjected to extraction with 1,2-dichloroethane, and the organic solvent was concentrated. Water was added to the concentrated solution, and the residual organic solvent was removed through distillation, to thereby obtain 13.7 g of m-cyanobenzyl acetate (yield 78%). The purity of the product was 97%.

As described hereinabove, according to the present invention, cyanobenzyl compounds such as cyanobenzyl alcohol compounds, cyanobenzyl halide compounds, and cyanobenzyl acyloxy compounds can be produced in a convenient manner at high yield and high purity from a cyanobenzylamine compound which is easily obtained from a phthalonitrile compound and an inexpensive nitrite salt.

While the invention has been described in detail and with reference to specific embodiments thereof, it will be apparent to one skilled in the art that various changes and modifications can be made therein without departing from the spirit and scope thereof.

What is claimed is:

1. A process for producing a cyanobenzyl compound comprising transforming an aminomethyl group of a cyanobenzylamine compound into a hydroxymethyl group, a halomethyl group, or an acyloxymethyl group without causing damage to a cyano group on the benzene ring.

2. A process for producing a cyanobenzyl compound according to claim 1, wherein the aminomethyl group is transformed into a hydroxymethyl group, a halomethyl group, or an acyloxymethyl group by use of nitrosonium ions.

3. A process for producing a cyanobenzyl compound according to claim 2, wherein the process includes generating nitrosonium ions from a nitrite salt under acidic conditions.

4. A process for producing a cyanobenzyl compound according to claim 2, wherein the process includes generating nitrosonium ions from a nitrogen oxide.

5. A process for producing a cyanobenzyl compound according to claim 1, wherein the reaction is carried out in the presence of a polar solvent.

6. A process for producing a cyanobenzyl compound according to claim 2, wherein the reaction is carried out in the presence of a polar solvent.

7. A process for producing a cyanobenzyl compound according to claim 3, wherein the reaction is carried out in the presence of a polar solvent.

8. A process for producing a cyanobenzyl compound according to claim 4, wherein the reaction is carried out in the presence of a polar solvent.

9. A process for producing a cyanobenzyl compound according to claim 1, wherein the cyanobenzylamine compound is represented by the following formula (I):

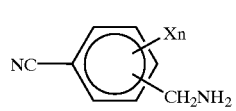

(I)

wherein each of —CH$_2$NH$_2$ and —X represents a substituent on the benzene ring; —CH$_2$NH$_2$ is bonded to the m- or p- position with respect to —CN; X represents a chlorine atom or a fluorine atom; n is an integer between 0 and 4 inclusive; and when n is 2 or more, the plurality of X's may be identical to or different from one another; and the cyanobenzyl compound is represented by the following formula (II):

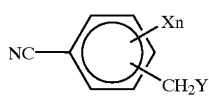

wherein each of —X and —CH₂Y represents a substituent on the benzene ring; —CH₂Y is bonded to the m- or p- position with respect to —CN; X represents a chlorine atom or a fluorine atom; n is an integer between 0 and 4 inclusive; and when n is 2 or more, the plurality of X's may be identical to or different from one another; Y represents a hydroxyl group, a fluorine atom, a chlorine atom, a bromine atom, an iodine atom, or an acyloxy group represented by —OCOR, wherein R represents a $C_1$–$C_8$ alkyl group, an alkenyl group, or an aryl group.

10. A process for producing a cyanobenzyl compound according to claim 2, wherein the cyanobenzylamine compound is represented by the following formula (I):

wherein each of —CH₂NH₂ and —X represents a substituent on the benzene ring; —CH₂NH₂ is bonded to the m- or p- position with respect to —CN; X represents a chlorine atom or a fluorine atom; n is an integer between 0 and 4 inclusive; and when n is 2 or more, a plurality of X's may be identical to or different from one another; and the cyanobenzyl compound is represented by the following formula (II):

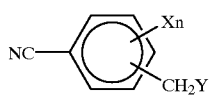

wherein each of —X and —CH₂Y represents a substituent on the benzene ring; —CH₂Y is bonded to the m- or p- position with respect to —CN; X represents a chlorine atom or a fluorine atom; n is an integer between 0 and 4 inclusive; and when n is 2 or more, the plurality of X's may be identical to or different from one another; Y represents a hydroxyl group, a fluorine atom, a chlorine atom, a bromine atom, an iodine atom, or an acyloxy group represented by —OCOR, wherein R represents a $C_1$–$C_8$ alkyl group, an alkenyl group, or an aryl group.

11. A process for producing a cyanobenzyl compound according to claim 9, wherein the cyanobenzylamine compound represented by formula (I) is p-cyanobenzylamine or m-cyanobenzylamine, and the cyanobenzyl compound represented by formula (II) is a corresponding p-cyanobenzyl alcohol or m-cyanobenzyl alcohol.

12. A process for producing a cyanobenzyl compound according to claim 10, wherein the cyanobenzylamine compound represented by formula (I) is p-cyanobenzylamine or m-cyanobenzylamine, and the cyanobenzyl compound represented by formula (II) is a corresponding p-cyanobenzyl alcohol or m-cyanobenzyl alcohol.

13. A process for producing a cyanobenzyl compound according to claim 9, wherein the cyanobenzylamine compound represented by formula (I) is p-cyanobenzylamine or m-cyanobenzylamine and the cyanobenzyl compound represented by formula (II) is a corresponding p-cyanobenzyl chloride, p-cyanobenzyl bromide, m-cyanobenzyl chloride, or m-cyanobenzyl bromide.

14. A process for producing a cyanobenzyl compound according to claim 10, wherein the cyanobenzylamine compound represented by formula (I) is p-cyanobenzylamine or m-cyanobenzylamine and the cyanobenzyl compound represented by formula (II) is a corresponding p-cyanobenzyl chloride, p-cyanobenzyl bromide, m-cyanobenzyl chloride, or m-cyanobenzyl bromide.

15. A process for producing a cyanobenzyl compound according to claim 9, wherein the cyanobenzylamine compound represented by formula (I) is p-cyanobenzylamine or m-cyanobenzylamine and the cyanobenzyl compound represented by formula (II) is a corresponding p-cyanobenzyl acetate or m-cyanobenzyl acetate.

16. A process for producing a cyanobenzyl compound according to claim 10, wherein the cyanobenzylamine compound represented by formula (I) is p-cyanobenzylamine or m-cyanobenzylamine and the cyanobenzyl compound represented by formula (II) is a corresponding p-cyanobenzyl acetate or m-cyanobenzyl acetate.

17. A cyanobenzyl compound which is produced through the process as recited in claim 1, wherein an aminomethyl group of a cyanobenzylamine compound is transformed into a hydroxymethyl group, a halomethyl group, or an acyloxymethyl group without damaging a cyano group on the benzene ring.

18. A cyanobenzyl compound which is produced through the process as recited in claim 2, wherein an aminomethyl group of a cyanobenzylamine compound is transformed into a hydroxymethyl group, a halomethyl group, or an acyloxymethyl group without causing damage to a cyano group on the benzene ring.

* * * * *